United States Patent [19]

Shimada

[11] Patent Number: 5,931,806
[45] Date of Patent: Aug. 3, 1999

[54] ACUPRESSURE-TYPE MOXA TREATMENT DEVICE

[76] Inventor: Osamu Shimada, 996 Shima-machi, Kumamoto City, Kumamoto Pref., Japan

[21] Appl. No.: 09/024,348

[22] Filed: Feb. 17, 1998

[30] Foreign Application Priority Data

Feb. 19, 1997 [JP] Japan .................................. 9-035047

[51] Int. Cl.⁶ .............................. A61M 37/00; A61F 7/00
[52] U.S. Cl. ................. 604/24; 607/96; 604/291
[58] Field of Search .................. 604/24, 291; 607/96, 607/114

[56] References Cited

U.S. PATENT DOCUMENTS

| | | | |
|---|---|---|---|
| 3,946,733 | 3/1976 | Han | 604/24 |
| 4,203,438 | 5/1980 | Shiu | 604/24 |
| 4,604,088 | 8/1986 | Nottbohm | 604/24 |
| 4,671,788 | 6/1987 | Wu | 604/24 |
| 4,731,050 | 3/1988 | Harada et al. | 604/24 |

*Primary Examiner*—Francis J. Jaworski
*Attorney, Agent, or Firm*—Marshall, O'Toole, Gerstein, Murray & Borun

[57] ABSTRACT

An acupressure-type moxa treatment device uses a carbonized moxa, of which main component is moxa and which is compression-moulded into a fixed shape and does not generate smoke nor bad smell when burned. The device includes a holding cage held between a front inner cylinder 1 and a rear inner cylinder 2, and an ignited carbonized moxa 9 in a holding cage 8. The inner cylinders enclosed by a cap 5, a front outer cylinder 2, and a rear outer cylinder 2. The front inner cylinder 1, the rear inner cylinder 2, the front outer cylinder 3, and the rear outer cylinder 2 are provided with cooperating and adjustable air inlets 1a, 2a, and air control ports 3a, 4a, respectively, to enable proper combustion of the carbonized moxa 9.

9 Claims, 6 Drawing Sheets

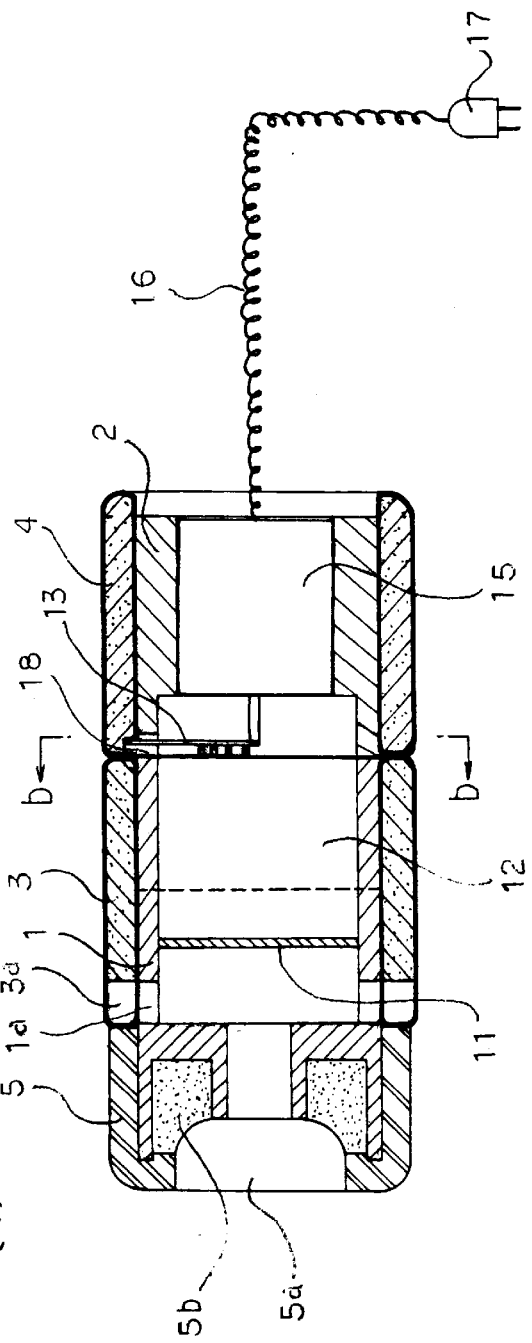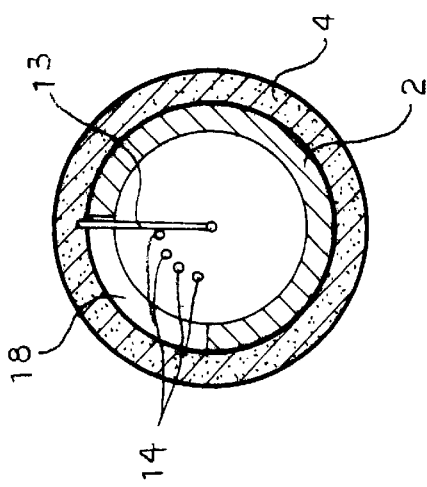
FIG. 8

PRIOR ART

ACUPRESSURE-TYPE MOXA TREATMENT DEVICE

FIELD AND BACKGROUND OF INVENTION

The present invention relates to an acupressure-type moxa treatment device that also exhibits therapeutic effects of acupressure.

The conventional acupressure-type moxa treatment device of this kind has a structure as shown in FIG. 9, wherein an inner cylinder having a cavity for loading moxa is provided. A bar-shaped moxa 51, which is moulded into a round bar of which the major component is leaves of mugwort, is ignited at the top end thereof and inserted into a front cylinder 52 from the back end thereof, and an appropriate amount of air for combustion is fed to the ignited portion of the moxa through air inlets 52a, 53a to maintain stable combustion of the bar-shaped moxa 51. The exteriors of the front inner cylinder 52 and the rear inner cylinder 53 are surrounded by a front outer cylinder 54 and a rear outer cylinder 55 respectively. Moreover, the outer circumferential surfaces of the respective outer cylinders are covered with heat-insulating material layers 56, 57 so that the therapist can hold the outer cylinder by hand and handle the device easily and freely. Thermic rays of moxabustion generated by the combustion of the bar-shaped moxa 51 are radiated through an opening 58a in the front end of a cap 58 towards the affected part. 59 is a heat insulator, 60 is a partition wall and 61 is a pipe. 62 is a moxa support portion that stabilizes the bar-shaped moxa 51 relative to the moxa treatment device. The front outer cylinder 54 and the rear outer cylinder 55 are provided with air control ports 54a. These outer cylinders can be rotated over corresponding inner cylinders to make these air control ports and the air inlets 52a, 53a provided in the sides of the inner cylinders 52, 53 work together to regulate the passage of air for combustion.

When the above-mentioned acupressure-type moxa treatment device is used to repeatedly give thermotherapy to the affected part, the bar-shaped moxa 51 will be consumed and its overall length will gradually get shorter. The bar-shaped moxa 51 will be pressed further forward into the inner cylinder and subsequently unloaded so powdery ashes of moxa accumulated inside can be removed and a fresh bar-shaped moxa 51 can be loaded.

The major component of the bar-shaped moxa 51 used in the conventional acupressure type moxa treatment device is moxa, which is normally produced by drying leaves of mugwort and rumpling the dried leaves with the fingers to refine them into cotton-like substance. This substance is then processed and turned into flakes or grains. Other materials that have proved to have beneficial effects may be used as supplementary components. Appropriate portions of these materials are mixed together, and wrapped in a sheet of paper (such as a kind of Japanese paper that does not produce an unpleasant odor when burned) to form the bar-shaped moxa. This bar-shaped moxa is loaded in a moxa treatment device such as one shown in the diagram and in the manner as illustrated in the diagram and used as the fuel of the acupressure-type moxa treatment device.

The use of the conventional form of moxa of a moxa treatment device in the abovementioned conventional configuration generates a large volume of smoke and unpleasant odor. These were proved to be causes of asthma attack in asthmatic patients who received moxabustion treatments. It was a problem because the smoke and odor might cause pain to asthmatic patients, the number of which has been increasing with recent environmental pollution. Japanese Utility Model No. HEI 7-31050 proposed improvements in the moxa itself, decreasing significantly the generation of smoke or bad smell, while maintaining the effects of the conventional moxabustion treatment.

This improvement will be explained briefly. The improved moxa does not differ from the conventional one in the sense that it uses, as the main component, the conventional moxa, which is prepared by drying leaves of mugwort and rumpling the dried leaves with the fingers to refine them into a cotton-like substance. This moxa is then subjected to dry distilling in an atmosphere of an inert gas, and carbonized. A binder is added to a mixture of this carbonized moxa and activated powder. The mixture is kneaded and moulded into a bar. A bar-shaped moxa is produced, which does not differ at all in appearance from the conventional bar-shaped moxa.

As mentioned before, this bar-shaped moxa does not differ externally from the conventional products, and can be directly used in the conventional acupressure-type moxa treatment device (for example, the device of FIG. 8). Moreover, the improved moxa has the following outstanding merits in its effects relative to the conventional moxa:

a) As carbonized moxa (that is, moxa dry-distilled in an inert gas) and activated charcoal powder are used as the materials, the improved moxa generates less smoke and bad smell when it is burnt. Moreover, because of the properties of the above-mentioned materials, the combustion process of the improved moxa is similar to that of charcoal and can maintain a combustion that has highly stable caloric force and temperature. As a result, the improved moxa can realize a state that promotes the generation of far-infrared rays.

b) As the materials are kneaded, bound, and moulded into a certain shape, it is easy to handle as a product.

c) As the ashes of the improved moxa retain the shape of the moulding without crumbling, the ashes do not scatter. Hence, there is reduced danger of burns, fire, etc.; cleaning is simpler; and the device itself is safer.

When the above-mentioned moxa (carbonized moxa) described in Provisional Utility Model HEI 7-31050 is used in an acupressure-type moxa treatment device of the conventional form to give thermotherapy, the following problems will be encountered:

1) When the combustion depletes the moxa after the top end of the bar-shaped moxa has been ignited, the bar-shaped moxa has been inserted deep into the inner cylinder of the moxa treatment device, and the burning moxa has radicled thermic rays of moxabustion are radiated towards the affected part, it will become necessary to push the bar-shaped moxa forward to keep the moxa burning in an optimal position and ensure stable combustion of the moxa. Estimating the distance the moxa should be pushed forward is extremely difficult because it is hard to judge the present position. Accordingly, it is done almost by a trial-and-error method.

2) To know exactly the state of depletion of the bar-shaped moxa, the bar-shaped moxa must be withdrawn from the inner cylinder. This is extremely inconvenient. If the moxa is not withdrawn, it will be difficult to know the exact remaining quantity of the moxa, and this in turn may hinder systematic execution of the therapy.

3) In giving thermotherapy, the difficulty in predicting the rate of depletion of the moxa makes it difficult to predict the time required for the treatments and to create a systematic therapy plan. As a result, scientific processing of the therapy cannot be made smoothly.

SUMMARY OF THE INVENTION

The present invention was made in view of the above-mentioned problems, and is intended to provide an acupressure-type moxa treatment device that uses carbonized moxa that generates little smoke or odor during combustion, said acupressure-type moxa treatment device being designed for simple and easy handling of moxa. In particular, carbonized moxa can be loaded into and unloaded from the moxa treatment device easily, the ashes generated by combustion can be removed easily, and other works are simplified and facilitated. Further, predicting the amount of moxa required for a given work load of thermotherapy and the required time is facilitated, and the processes of igniting and combusting the fuel are generally simple and easy.

Another objective of the present invention is to provide an acupressure-type moxa treatment device that is of a simple construction, can be easily opened and assembled, and can be easily maintained after use.

To solve the above-mentioned problems, this acupressure-type moxa treatment device comprises an inner cylinder wherein a front inner cylinder has an opening for radiating thermic rays of moxabustion in the front end thereof and plural air inlets in sides thereof The device also has a rear inner cylinder having the same outer diameter as said front inner cylinder, an opening for an air passage in the rear end thereof, and plural air inlets in the sides thereof in the longitudinal direction to form a middle block into which a fuel cage is inserted and held. A heat-resistant elastic cap is mounted on the front end of the inner cylinder, and has an opening for passing thermic rays of moxabustion in the front end thereof. A front outer cylinder is placed over the outer circumferential surface of the inner cylinder near the middle in the longitudinal direction thereof, and has plural air control ports in the sides that cooperate with the air inlets provided in sides of the front inner cylinder when the front outer cylinder is rotated relative to the inner cylinder to adjust the level of air passage. A rear outer cylinder is placed over the rear portion of the outer circumferential surface of the inner cylinder and has plural air control ports in the sides that cooperate with the air inlets provided in sides of the rear inner cylinder when the rear outer cylinder is rotated relative to the inner cylinder to adjust the level of air passage. A carbonized moxa holding cage can be inserted into or taken out of the space formed between the front inner cylinder and the rear inner cylinder, which is enclosed by a porous circumferential wall such as punched metal, to supply air from outside through said circumferential wall to enable combustion of the carbonized fuel therein. Carbonized moxa is loaded in said carbonized moxa holding cage to be ignited and burnt therein, the moxa having been char dry-distilled in an atmosphere having an inert gas as the main component and then compression-moulded into a form of briquette or honeycomb.

To give thermotherapy to an affected part with the acupressure-type moxa treatment device of the above-mentioned construction, the heat-resistant elastic cap is first securely mounted on the front end of the front inner cylinder. Next, the front outer cylinder is placed over the front inner cylinder from the rear thereof, and the front outer cylinder is pushed till the front end of the outer cylinder comes to a close contact with the rear end of the cap. In this process, the polar symmetric positions of the front outer cylinder and the front inner cylinder are adjusted so that the plural air control ports provided in the front end of the front outer cylinder are positioned to mutually interfere with the plural air inlets provided on sides of the front inner cylinder. Next, the carbonized moxa holding cage is opened, a carbonized moxa which has been ignited at one end is loaded into the cage, and the cage is closed to form an integral assembly.

This carbonized moxa holding cage may be constructed, for example, in such a way that one part of the cage is a cover of the other part of the cage, and the cover part is screwed into the other part, and conversely the cover is unscrewed to open the cage. Such an arrangement eliminates inadvertent opening of the cover and unloading of the burning carbonized moxa. Thus, safe execution of therapy is assured. The cage for holding the ignited carbonized moxa is placed in the space formed at the rear of the front inner cylinder, then the rear inner cylinder is inserted in a position enclosing the carbonized moxa holding cage. Thus, the carbonized moxa holding cage is positioned at the front and at the rear by the pair of inner cylinders.

Next, the rear outer cylinder is placed over the circumferential surface of the rear inner cylinder, and the rear outer cylinder is pressed till the front end of the rear outer cylinder come to a close contact with the rear end of the front outer cylinder. In the process, the polar symmetric positions of the rear outer cylinder and the rear inner cylinder are adjusted so that the plural air control ports provided in the front end of the rear outer cylinder are positioned to mutually interfere with the plural air inlets provided on sides of the rear inner cylinder, just in the same manner as the adjustment of positions of the air inlets and air control ports of the front inner cylinder and the front outer cylinder explained above.

When the moxa treatment device is in the above-mentioned state, the air flow rate from the opening in the rear end of the rear inner cylinder is regulated by adjusting the air flow by controlling the degree of opening of the air control ports of the front outer cylinder and the rear outer cylinder to maintain the desired combustion of the carbonized moxa. In this way, the thermic rays of moxabustion being radiated from the front end of the front inner cylinder can be freely directed onto the affected part to give appropriate treatment.

The outer circumferential surfaces of the front outer cylinder and the rear outer cylinder or the outer circumferential surface of the cap, or the outer circumferential surfaces of both the outer cylinders and the cap may be covered with heat-insulating material layers. This is effective in preventing accidents that might otherwise occur when handling the moxa treatment device for thermotherapy, such as a burn on the skin of the hand that holds the moxa treatment device, due to abnormal rise in temperature on the surface of the moxa treatment device.

The cage for holding carbonized moxa may be provided with a pillar inside the rear chamber so that the cage has a reinforced structure that can endure external pressure.

BRIEF DESCRIPTION OF THE DRAWINGS

FIG. 8(a) is a sectional view of another embodiment of the acupressure-type moxa treatment device according to the present invention, and FIG. 8(b) is a sectional view along the line b—b of FIG. 8(a).

DETAILED DESCRIPTION OF THE INVENTION

Figure 1:
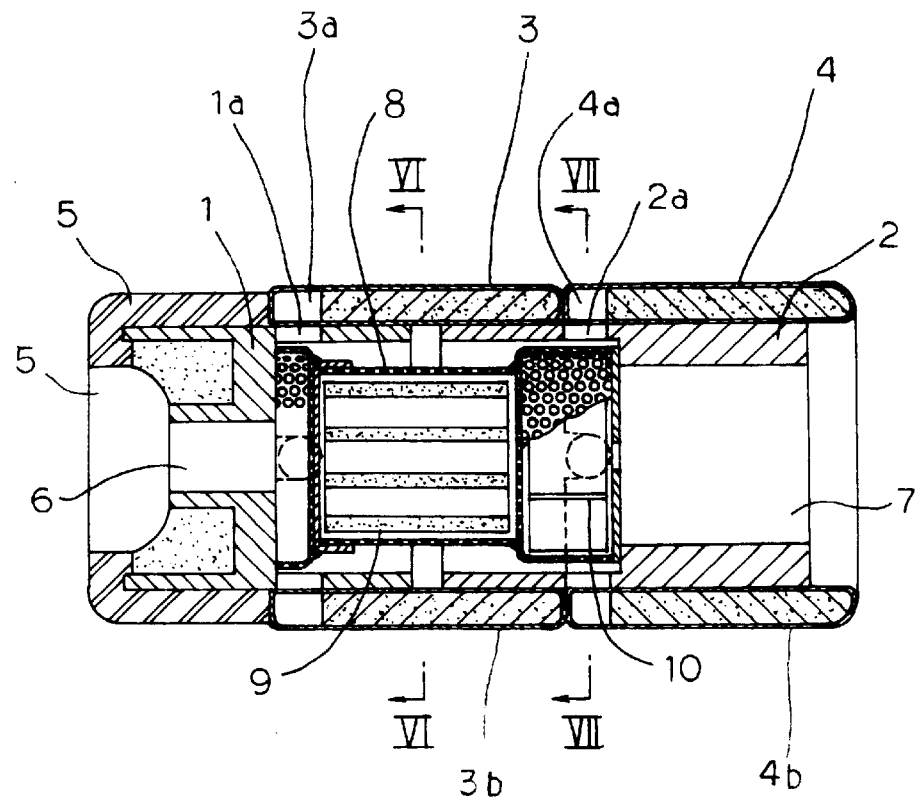
FIG. 1 is a sectional view of one embodiment of the acupressure-type moxa treatment device according to the present invention.
Figure 2:
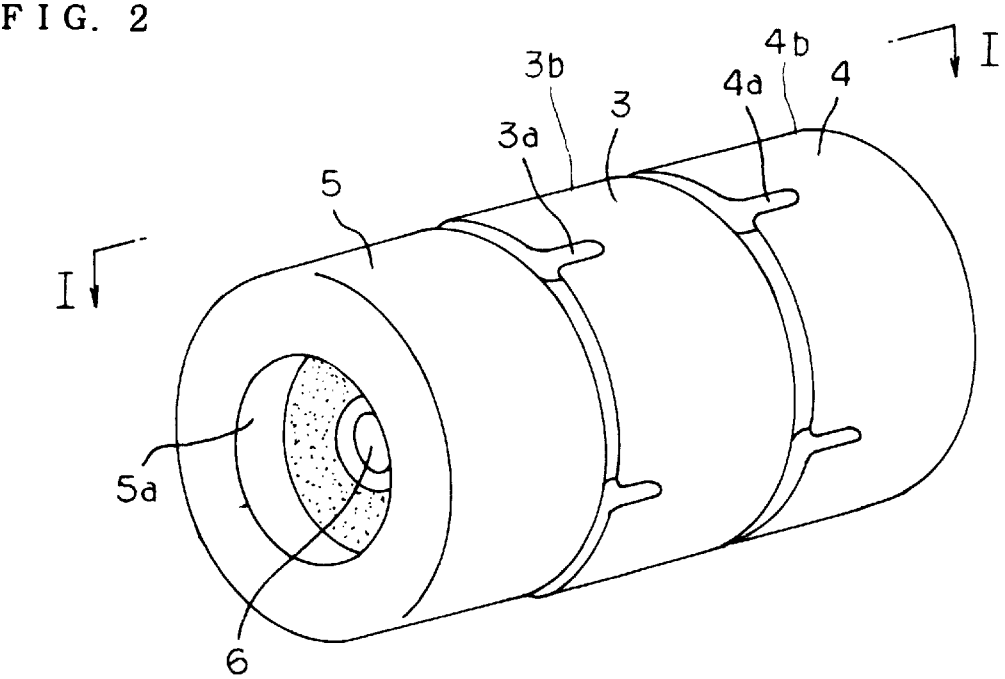
FIG. 2 is a perspective view of the acupressure-type moxa treatment device of FIG. 1.

With reference to FIG. 1 through FIG. 7, the manner of making and using an acupressure-type moxa treatment device according to the present invention will be described.

The acupressure-type moxa treatment device of the present invention is provided with an inner cylinder, which forms a place for combustion of a fuel loaded therein, and an outer cylinder, which externally holds the inner cylinder. The device is arranged so thermic rays of moxabustion radiate forward through an opening in a cap mounted on the front end of the inner cylinder. The inner cylinder comprises a front inner cylinder 1 having an opening 6 for radiating thermic rays of moxabustion from the front end, plural air inlets 1a (four in the illustrated embodiment) in the sides, a rear inner cylinder 2 having the same outer diameter as the front inner cylinder 1, an opening 7 for air passage in the rear end, and plural air inlets (four in the illustrated embodiment) in the sides. The air inlets are arranged in the longitudinal direction, and a fuel cage 8 is inserted and held in the middle portion of the inner cylinders.

The cap 5 is mounted on the front end of the inner cylinder, is provided with an opening 5a that allows the thermic rays of moxabustion to pass through the front end thereof, and is made of rubber or synthetic resin having heat resistance and elasticity. The outer cylinder comprises a front outer cylinder 3 placed over the approximate center, in the longitudinal direction, of the outer circumferential surface of the inner cylinder, and has plural air control ports 3a (four in the illustrated embodiment) in the sides that cooperate with the air inlets 1a provided in sides of the front inner cylinder when the front outer cylinder 3 is rotated relative to the inner cylinder to adjust the level of air passage. A rear outer cylinder 4 is placed over the rear portion of the outer circumferential surface of the inner cylinder and has plural air control ports 4a (four in the illustrated embodiment) in the sides that cooperate with the air inlets 2a provided in sides of the rear inner cylinder 2 when the rear outer cylinder 4 is rotated relative to the inner cylinder to adjust the level of air passage. The front outer cylinder 3 is covered with a heat-insulating material layer 3b to minimize the risk of accidents due to excessive rise in the temperature of said surface. Similarly, the rear outer cylinder 4 is covered with a heat-insulating material layer 4b. The outer circumferential surface of the cap 5 may also be covered in some cases.

The carbonized moxa holding cage 8 is of a two-part construction that can be inserted into or taken out of the space formed between the front inner cylinder and the rear inner cylinder, and is enclosed by a circumferential wall of punched metal to supply air from outside through said circumferential wall to enable the desired state of combustion of the carbonized moxa 9 therein. One example of the cage 8 is shown in detail in FIG. 4. A front cage 8a is made of punched metal, and is provided on the back side thereof with a mesh 8n for preventing ashes and the like of the carbonized moxa 9 from falling from the device. The mesh 8n is made of very fine metal wire (stainless steel in the illustrated embodiment), and with a flange 8b on the rear thereof A body 8c and a rear cage 8d are made of punched metal and are united. The body 8c is dimensioned to hold the carbonized moxa therein, and is also dimensioned to be stored in the flange 8b with the carbonized moxa 9 being held in the body 8c. The rear cage 8d has a sufficient space to hold a pillar 10. Rear cover 8e closes the rear cage 8d after the pillar 10 is held in the rear cage 8d. The rear cover 8e is provided with three paths (openings) 8f along a diameter. In the present embodiment, three paths 8f are used to set the duration of combustion of the carbonized moxa at about one hour. When the number of paths 8f is increased, the duration of combustion will be reduced. Conversely, when the number is decreased, the duration of combustion will be increased. Depending on the size of the opening, one path 8f might result in incomplete combustion.

The carbonized moxa 9, of which main component is char produced by dry-distilling moxa in an atmosphere of an inert gas, is compression-moulded into the form of a briquette. It is provided with holes 9a similar to those of the briquette.

The carbonized moxa 9 is loaded into the holding cage 8, then one end of the carbonized moxa 9 is ignited to burn. The carbonized moxa 9 is available in the compression-moulded state in the shape of a briquette as shown in the diagram. It is also available in the form of honeycomb.

The use of the acupressure-type moxa treatment device of the above-mentioned construction in providing thermo-therapy to a patient will be explained next. First, one end of the carbonized moxa 9 is ignited. The ignited carbonized moxa 9 is then loaded into the body 8c of the holding cage 8 (refer to FIG. 4). In that condition, the front end of the body 8c is pushed forward from the rear into the flange 8b. It is desirable to provide, between the flange 8b and the body 8c, a means for preventing easy disengagement. There are a variety of suitable means for doing this. For example, the difference between the outer diameter and the inner diameter of the respective parts may be minimized so that, once engaged, the parts can not be easily disconnected from each other. Alternatively, the ends of the flange 8b and the body 8c may be provided with protrusions or threads so that when they are pushed into engagement and turned relative to each other, they cannot be separated by merely pulling them away from each other. After the parts are engaged, the pillar 10 is loaded into the rear cage 8d, and the rear end of the rear cage 8d is closed with the rear cover 8e to complete the assembly of the holding cage 8.

Figure 3:
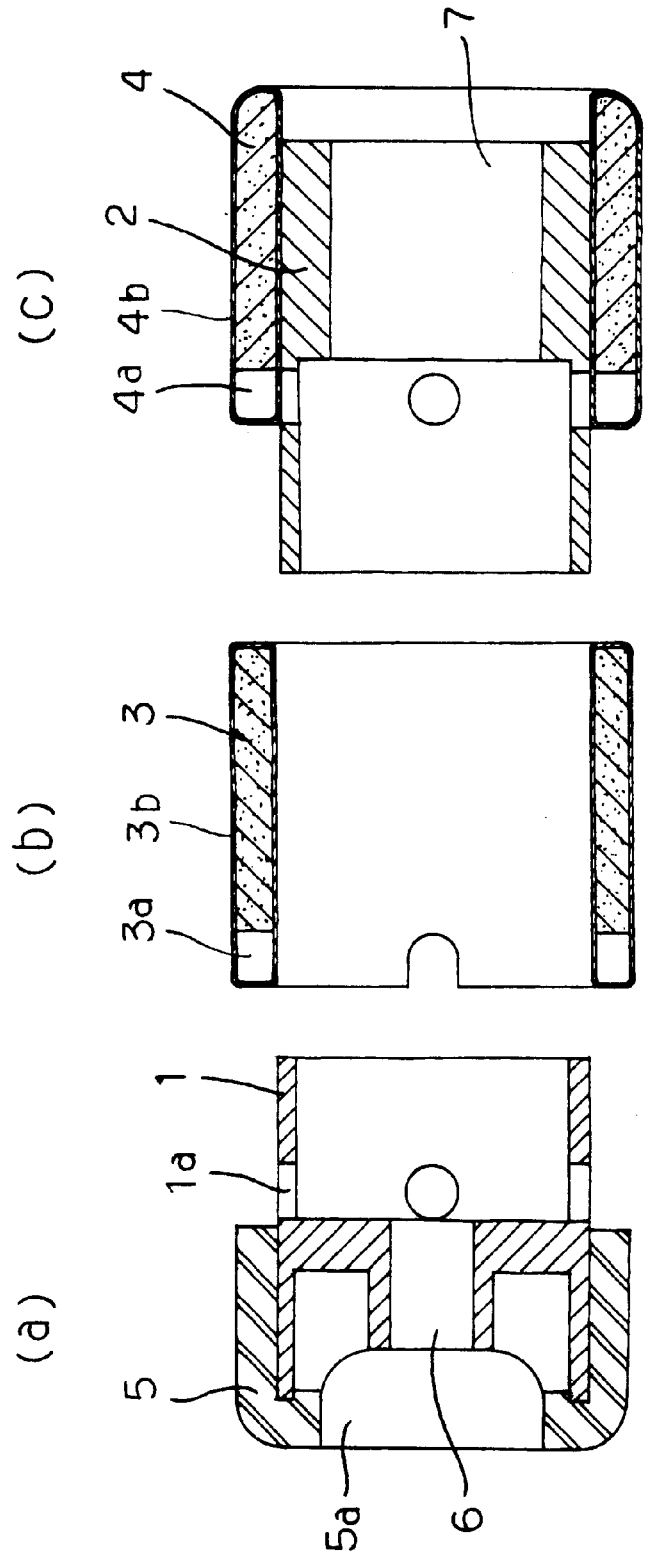
FIG. 3(a), FIG. 3(b), and FIG. 3(c) are sectional views of the respective blocks that constitute the body of the acupressure-type moxa treatment device of FIG. 1.
Figure 4:
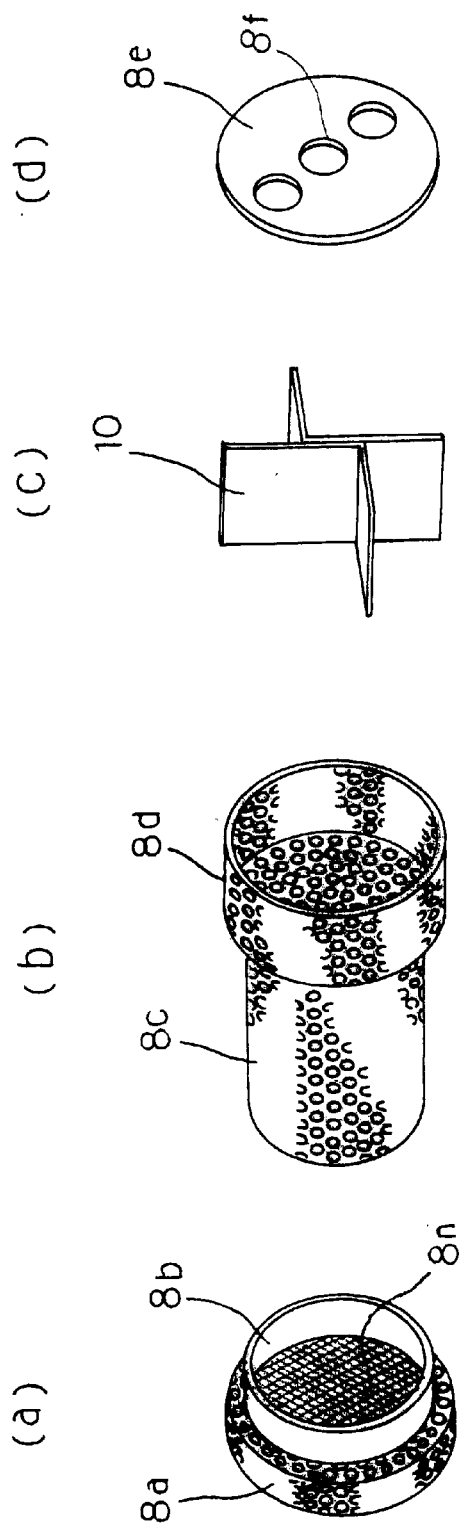
FIG. 4(a), FIG. 4(b), FIG. 4(c) and FIG. 4(d) are perspective views of the disassembled fuel cage of the acupressure-type moxa treatment device of FIG. 1.
Figure 5:
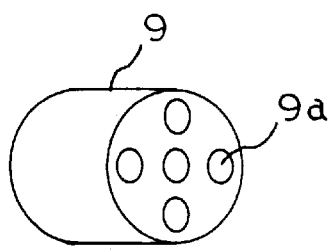
FIG. 5 is a perspective view of the carbonized fuel of the acupressure-type moxa treatment device of FIG. 1.
Figure 6:
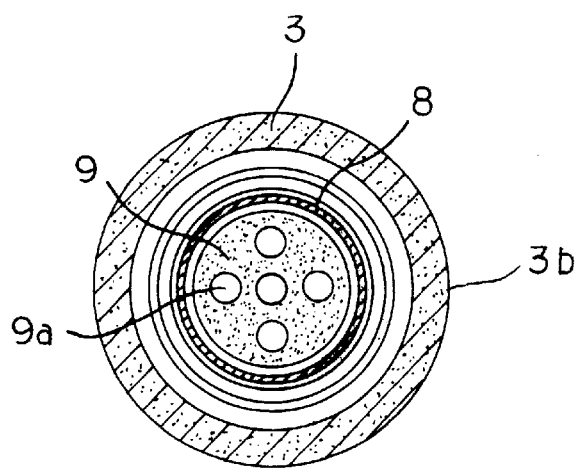
FIG. 6 is a sectional view along the line VI—VI of the acupressure-type moxa treatment device of FIG. 1.
Figure 7:
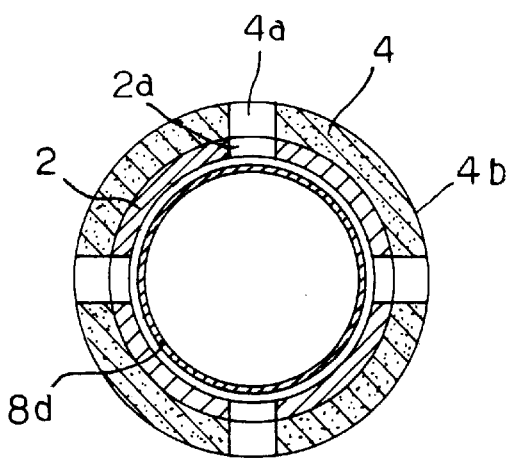
FIG. 7 is a sectional view along the line VII—VII of the acupressure-type moxa treatment device of FIG. 1.
Figure 9:
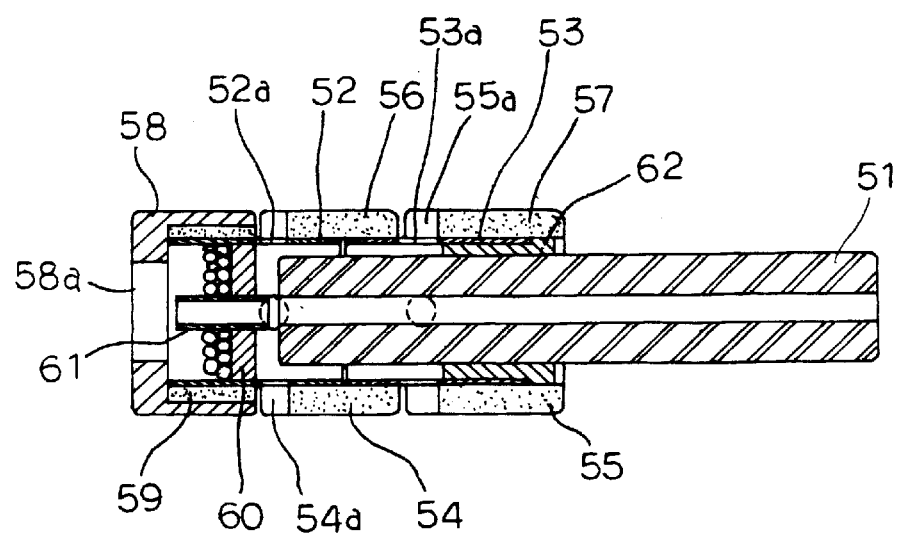
FIG. 9 is a sectional view of the conventional acupressure-type moxa treatment device.

The entirety of the acupressure-type moxa treatment device is assembled in the manner shown in FIG. 3. The assembled holding cage 8 with the ignited carbonized moxa 9 is loaded into the space in the front inner cylinder shown in the diagram, then the front outer cylinder 3 is mounted on the rear of the front inner cylinder 1. After that, the rear inner cylinder 2 shown in FIG. 3(c) is inserted together with the rear outer cylinder 4 into the front outer cylinder 3 to assemble the parts into an integral body. In this condition, the front outer cylinder 3 is relatively rotated over the front inner cylinder 1, or the rear outer cylinder 4 is relatively rotated over the rear inner cylinder 2, to control the inflow rate of air supplied through the holding cage 8 to the carbonized moxa 9 through the air inlets 1a, 2a provided in the sides of the inner cylinder and the air control ports 3a, 4a provided in the sides of the outer cylinder.

The point of time when the carbonized moxa 9 is completely burnt can be determined very easily and accurately be detecting the termination of radiation of thermic rays from the opening 6 or by timing the duration of the combustion of the carbonized moxa 9 against the time needed for full combustion, which may be calculated in advance. Replacement of the carbonized moxa 9 with a fresh moxa can be performed easily in a manner similar to that of the above-mentioned assembly. The ashes of the burnt fuel remain intact in the form of the moulding due to the work of the binder that was mixed at the time of the moulding. Hence, removal and disposal processes are quite simple.

FIG. 8 shows another embodiment of the acupressure-type moxa treatment device of the present invention. This embodiment of the acupressure-type moxa treatment device differs from the above-mentioned embodiment in that in place of the carbonized moxa 9, an electric heater 11 is used to electrically warm the affected part. 12 is a transformer, and when a rear outer cylinder 4 is rotated relative to a front outer cylinder 3, as shown in FIG. 8(b), the position of a contacting piece 13 relative to plural contacts 14 will be changed to control the heating temperature of the electric heater 11. Moreover, just like the above-mentioned embodiment, a medical liquid such as extract of loquat leaves may be impregnated in a moisture absorbent 5b (such as sponge and cotton wool) in a cap 5, and the liquid is made to be evaporated by the heat of the electric heater 11 or by the heat of the carbonized moxa, and this evaporated liquid is made to be absorbed by the affected part to exhibit efficacy such as pain killing. 1-5 is a safety device in which a thermostat and a fuse are provided. If the electric heater 11 generates excessive heat or a large current flows in the circuit, the safety device will break the circuit. The safety device 15 is stored in the rear inner cylinder 2, and is connected to a cord 16 and a plug 17 in this order. An arc-shaped notch 18 is formed in the rear inner cylinder 2 to allow the contacting piece 13 to turn. Parts common to those of the above-mentioned embodiment are denoted by the same marks, and explanation of these parts is omitted.

The acupressure-type moxa treatment device according to the present invention is constructed as mentioned above, and has the following effects:

The carbonized moxa is a moulding of moxa that is made in a fixed size of easy handling. Hence it is possible to make the carbonized moxa burn in an optimal position for automatic stable combustion of moxa. As a result, the conventional practice of igniting the top end of a bar-shaped moxa, inserting the ignited moxa deep into the inner cylinder of the moxa treatment device, and pressing the bar-shaped moxa forward to an optimal position with depletion of the moxa is not required. The inconvenience of the conventional device, which requires the distance over which the moxa should be pressed forward to be estimated nearly on a trial-and-error basis because the present state of depletion cannot be discerned, is eliminated. Moreover, it is possible to plan thermotherapy in a systematic manner, such plans including predictions of the consumption of moxa and of the time required for treatment.

In a more specific embodiment, the handling of the moxa treatment device is made with extra safety and ease, and the risk of accidents such as a burn that may be suffered by a handler due to rise in temperature on the surface of the moxa treatment device is reduced.

In a further embodiment, the strength of the carbonized moxa holding cage in the longitudinal direction of the moxa treatment device is increased.

What is claimed is:

1. An acupressure-type moxa treatment device in which fuel is stored and combusted in an inner cylinder that is held within an outer cylinder and thermic rays of moxabustion are radiated forward through an opening of a cap mounted on the top end thereof, said acupressure-type moxa treatment device comprising:

a front inner cylinder having an opening in the front end thereof for radiating thermic rays of moxabustion, and plural air inlets in sides thereof;

a rear inner cylinder having the same outer diameter as said front inner cylinder and having an opening for air passage in the rear end thereof and plural air inlets on the sides thereof;

the front and rear inner cylinders being arranged in a longitudinal direction to form a middle block into which a carbonized moxa holding cage can be inserted and held;

a heat-resistant elastic cap mounted at the front end of the inner cylinder and having an opening for passing thermic rays of moxabustion through the front end thereof;

a front outer cylinder placed over the outer circumferential surface of the inner cylinder near the longitudinal middle thereof having plural air control ports in the sides that cooperate with the air inlets on the sides of the front inner cylinder when the front outer cylinder is rotated relative to the inner cylinder to enable the level of air passage to be adjusted;

a rear outer cylinder placed over the rear portion of the outer circumferential surface of the inner cylinder and having plural air control ports in the sides that cooperate with the air inlets on the sides of the rear inner cylinder when the rear outer cylinder is rotated relative to the inner cylinder to enable the level of air passage to be adjusted;

a carbonized moxa holding cage sized to be insertable into or taken out of the space formed between the front inner cylinder and the rear inner cylinder and being enclosed by a porous circumferential wall to supply air from outside through said circumferential wall to enable combustion of the carbonized moxa therein; and a carbonized moxa having moxa char dry-distilled in an atmosphere of an inert gas as the main component, being compression-moulded into a form of briquette or honeycomb, and being sized to be loaded in said carbonized moxa holding cage to be ignited and burnt therein.

2. An acupressure-type moxa treatment device of claim 1 wherein the outer circumferential surface of said outer cylinder is covered with a heat-insulating material layer.

3. An acupressure-type moxa treatment device of claim 1 wherein the outer circumferential surface of said cap is covered with a heat-insulating material layer.

4. An acupressure-type moxa treatment device of claim 1 wherein the outer circumferential surface of said outer cylinder and the outer circumferential surface of said cap are covered with a heat-insulating material layer.

5. An acupressure-type moxa treatment device of claim 1 wherein a rear chamber of said carbonized moxa holding cage is provided with a pillar.

6. An acupressure-type moxa treatment device of claim 2 wherein a rear chamber of said carbonized moxa holding cage is provided with a pillar.

7. An acupressure-type moxa treatment device of claim 3 wherein a rear chamber of said carbonized moxa holding cage is provided with a pillar.

8. An acupressure-type moxa treatment device of claim 4 wherein a rear chamber of said carbonized moxa holding cage is provided with a pillar.

9. An acupressure-type moxa treatment device of claim 1 wherein the porous circumferential wall of the holding cage is made of punched metal.

* * * * *